United States Patent [19]
Sanchez

[11] Patent Number: 5,499,965
[45] Date of Patent: Mar. 19, 1996

[54] SHAPED LIFTING BELT AND METHOD

[75] Inventor: Ana V. Sanchez, Miami, Fla.

[73] Assignee: FLA Orthopedics, Inc., Fla.

[21] Appl. No.: 367,006

[22] Filed: Dec. 30, 1994

[51] Int. Cl.⁶ .................................................. A61F 5/00
[52] U.S. Cl. ..................... 602/19; 128/96.1; 128/100.1; 128/101.1; 128/106.1; 128/107.1; 2/235; 2/236; 2/237; 2/255; 2/319
[58] Field of Search ............................. 128/96.1, 100.1, 128/101.1, 106.1, 107.1; 2/255, 319, 235–237, 300, 311; 602/19

[56] References Cited

U.S. PATENT DOCUMENTS

| | | | |
|---|---|---|---|
| 5,040,524 | 8/1991 | Votel et al. | 602/19 |
| 5,148,549 | 9/1992 | Sydor | 128/845 X |
| 5,188,586 | 2/1993 | Castel et al. | 128/845 X |
| 5,257,419 | 11/1993 | Alexander | 602/19 X |
| 5,399,151 | 3/1995 | Smith | 602/19 |

Primary Examiner—Richard J. Apley
Assistant Examiner—Kim M. Lee
Attorney, Agent, or Firm—Jack E. Dominik

[57] ABSTRACT

A shaped lifting belt and method in which the shape is provided by deepening the central lumbar panel in the rear to a depth of at least an additional half of the depth of the side wraps, providing the lumbar panel with expandable elements, and then separating the ends of the wrap from the lumbar panel by shape panels which are stretchable and positioned to engage the upper rear portion of the hips is disclosed. The method of the invention requires the wearer to first engage the lifting belt assembly and secure the suspenders in the forward desirable position. Thereafter, the shape straps are secured to the inner portion of the wrap ends. The wrap ends are then secured to a central portion of the body followed by substantially encircling the same with the side pulls. Where coloring is desired, the suspender assembly may be of a different color than the belt itself, and optionally a removable side pull may be color coded or otherwise decorated to suit the application.

8 Claims, 5 Drawing Sheets

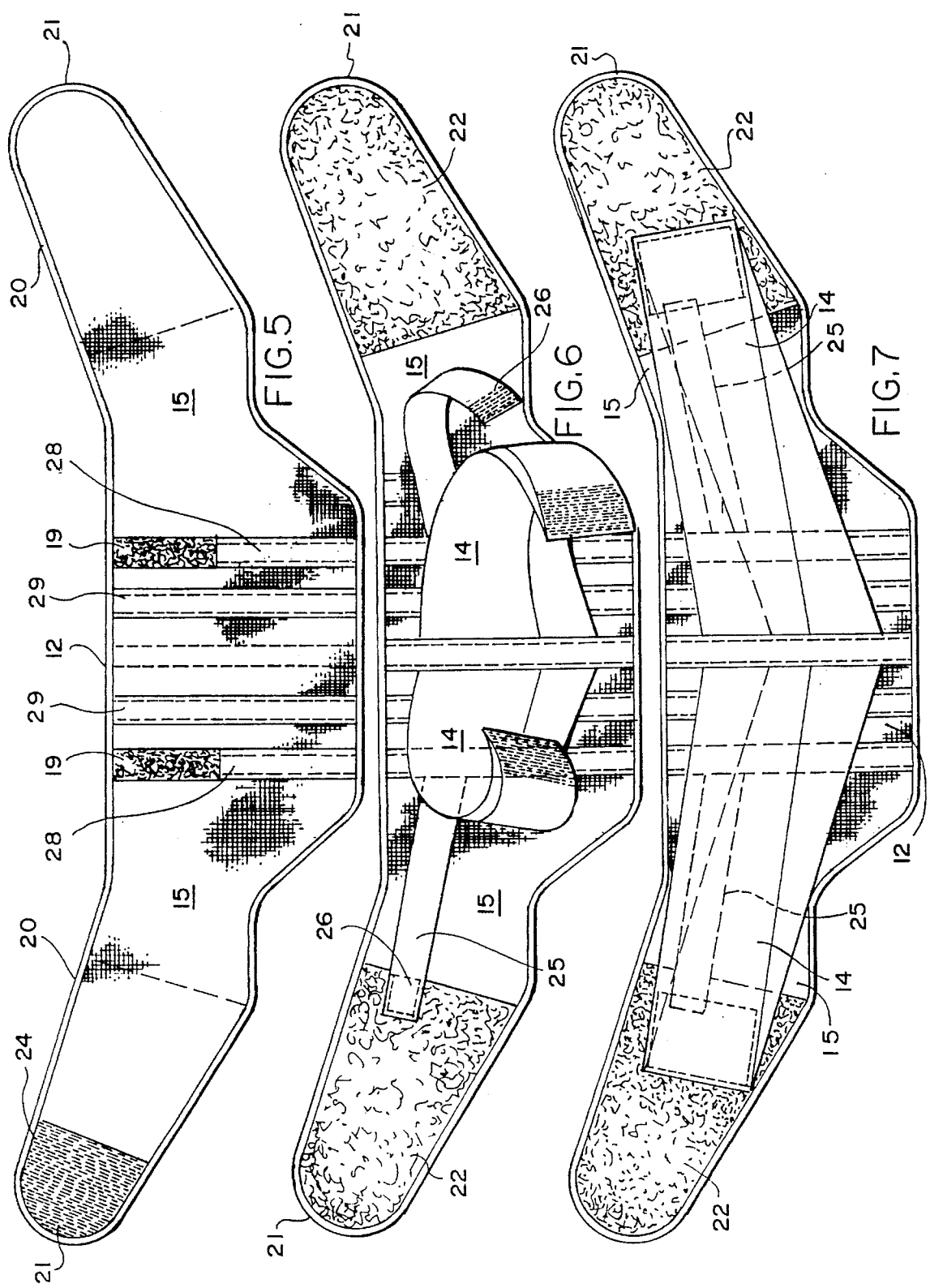

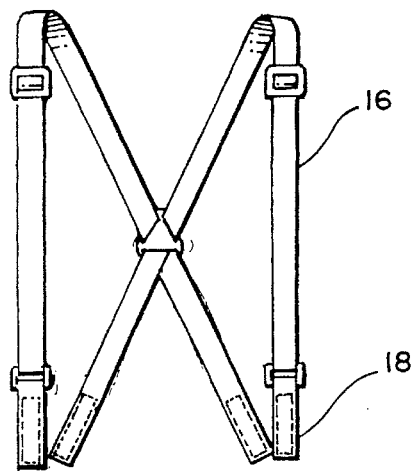
FIG. 8
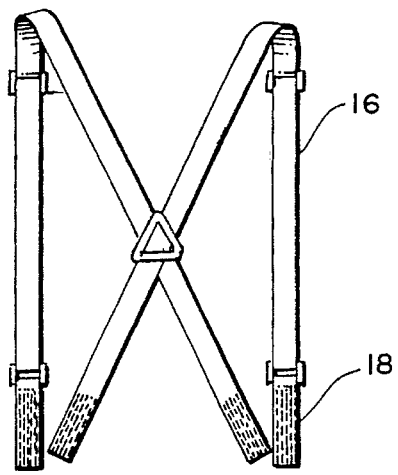
FIG. 9
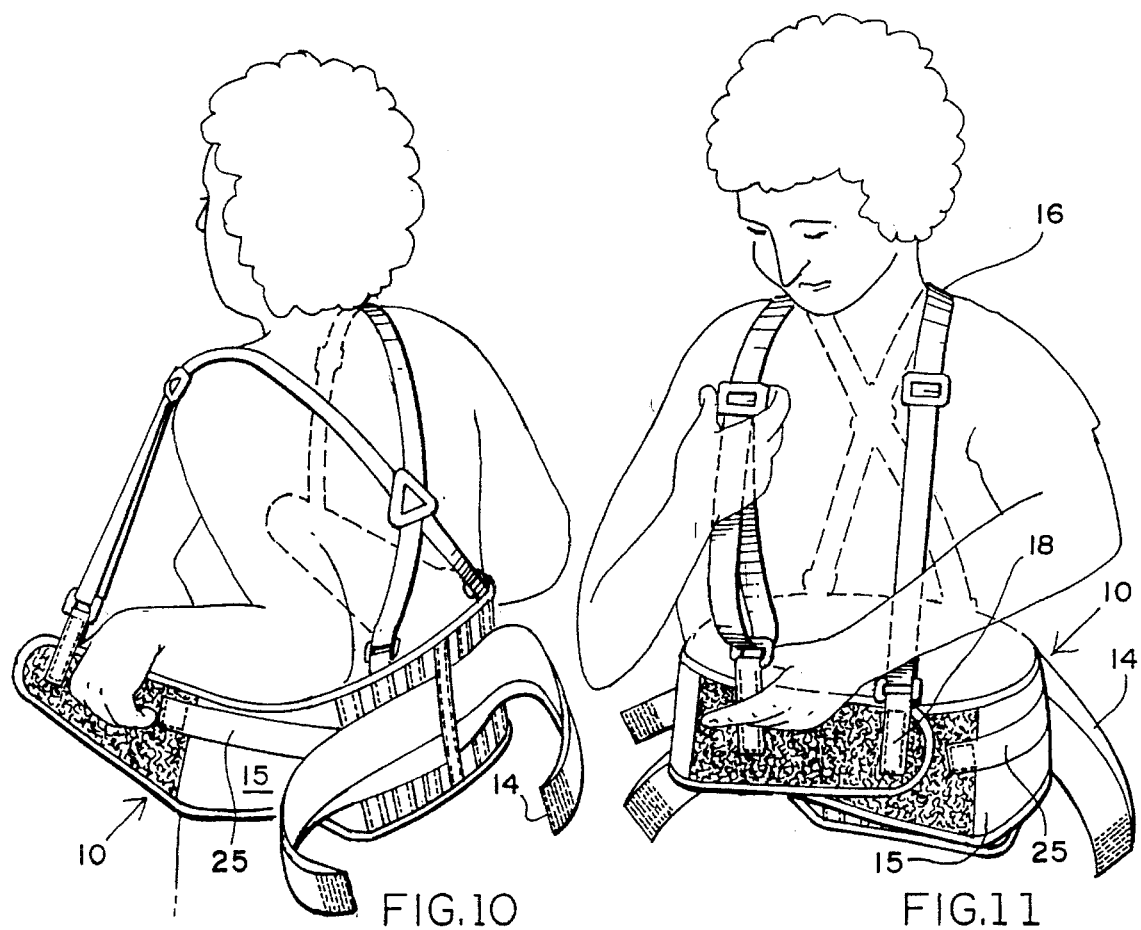
FIG. 10
FIG. 11

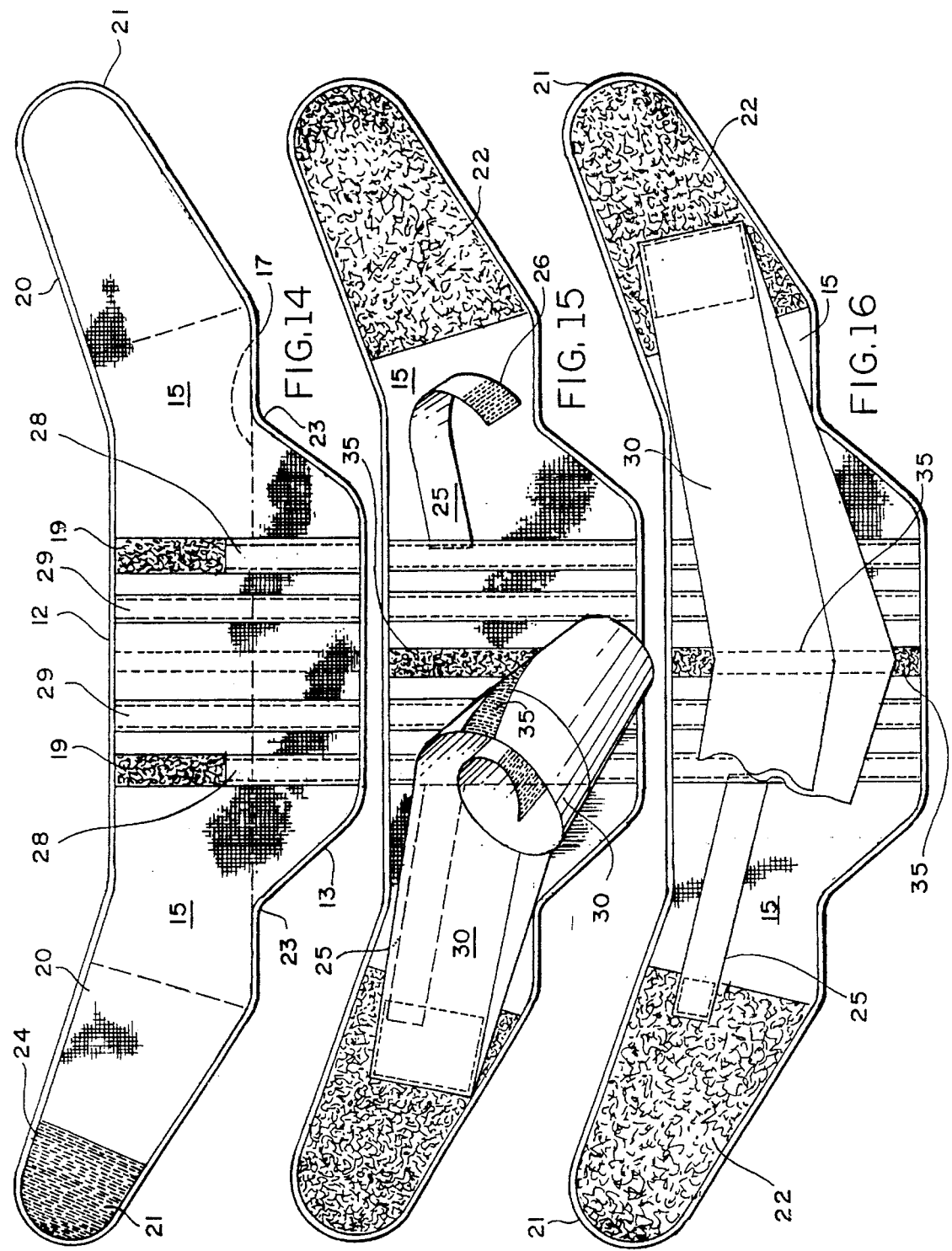

SHAPED LIFTING BELT AND METHOD

FIELD OF THE INVENTION

The present invention is directed to the subject matter of lifting belts used by people who are lifting various loads such as warehouseman, hospital attendants, nursing school teachers, and the like. It is specifically directed, however, to such persons where the hips are somewhat larger than the torso.

SUMMARY OF THE PRIOR ART

The prior art is exemplified by U.S. Pat. Nos. 5,040,524; 5,148,549. These patents and their commercial embodiments find utility on suppressing the tendency of persons lifting loads, particularly in awkward positions, from acquiring back strains and injuries.

More specifically, the lifting belt and method of U.S. application Ser. No. 08/118,889 filed Sep. 10, 1993, is addressed to the subject matter of various sizes of persons who might use a lifting belt. But it is not directed to those whose size may be shaped with larger hips than the torso, typically a female but not necessarily.

Accordingly it becomes highly desirable to develop a lifting belt and develop it to shape the belt to conform to a larger hip size.

SUMMARY OF THE INVENTION

The present invention is directed to a shaped lifting belt and method in which the shape is provided by deepening the central lumbar panel in the rear to a depth of at least an additional half of the depth of the side pulls, providing the lumbar panel with expandable elements, and then separating the ends of the wrap from the lumbar panel by shape panels which are stretchable and positioned to engage the upper rear portion of the hips. Additionally a shape strap is provided and secured to the lumbar panel at its upper outward extremities and made of a semi-inflexible material, but spanning the shape panel and removably securable to the interior portion of the wrap ends. Removable suspenders are provided with two fixed spots and the rear portion of the belt assembly over the laterally outer spaced stays of the lumbar panel. Interiorly of the wrap provision is made for the shape pulls to anchor themselves forwardly on the interior portion of the wrap and thereby shape the shape panel to fit the hips. Optionally the side pulls are removable. The method of the invention requires the wearer to first engage the lifting belt assembly and secure the suspenders in the forward desirable position. Thereafter, the shape straps are secured to the inner portion of the wrap ends. The wrap ends are then secured to a central portion of the body followed by substantially encircling the same with the side pulls. Where coloring is desired, the suspender assembly may be of a different color than the belt itself, and optionally a removable side pull may be color coded or otherwise decorated to suit the application.

In view of the foregoing it is a principal object of the present invention to provide a shaped lifting belt with a shaping strap and shaping panel which will permit the user to adjust the belt assembly when secured to accommodate the hips and more particularly the upper portion of the hips.

Yet another object of the present invention is to provide a shaped lifting belt in which the suspenders may be adjusted at the forward portion to accommodate various chest and breast sizes.

An additional object of the present invention is to achieve the above objectives with a structure that permits decorator stylization with the suspender assembly or with a removable side pull or a combination of both.

Yet another object of the present invention is to achieve all of the foregoing advantages with a cost effective construction.

BRIEF DESCRIPTION OF THE DRAWINGS

The foregoing objects and advantages will be better understood as the following description proceeds, taken in conjunction with the accompanying illustrative drawings, in which:

FIG. 5 is a plan view of the subject belt with the suspender assembly removed and showing the rear portion thereof with the removable attachments for the rear portion of the suspender assembly;

FIG. 6 is a reverse side view of the shaped belt of FIG. 5 showing the side pulls, and shape straps in their partially removed position from the belt itself;

FIG. 7 is a plan view of the portion of the inside of the shaped lifting belt of FIG. 6 with the side pull and shape straps in place;

FIG. 8 is a plan view of the suspender assembly with the hook ends shown in phantom lines;

FIG. 9 is a view similar to that of FIG. 8 but showing the hook ends of the suspender assembly;

FIG. 10 is a partially diagrammatic view of a person commencing to wrap the shaped lifting belt around her upper hip portion;

FIG. 1 is a view sequential to that of FIG. 10 showing the adjustment of the suspender assembly and showing the side pulls and shape straps in a partially disconnected configuration;

FIG. 14 is a view comparable to that of FIG. 5 but showing the provision for a removable side pull;

FIG. 15 is a view comparable to that of FIG. 16 but showing the removable side pull in exploded relationship to the back of the belt and showing the shape strap comparable to its showing in FIG. 6; and FIG. 16 is a plan view of the exterior portion of the belt with the removable side pull shown in position and the shape strap shown in position.

DESCRIPTION OF PREFERRED EMBODIMENT

Figure 1:
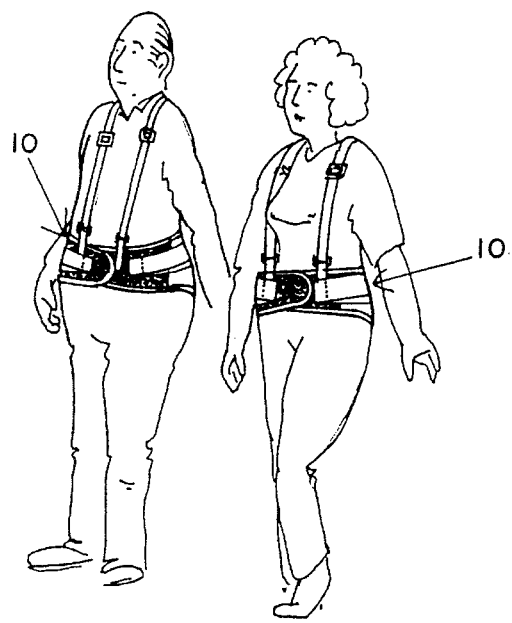
FIG. 1 illustrates two persons side-by-side, one male and one female, utilizing the subject shaped lifting belt to accommodate hip sizes larger than that of the torso.

The shaped lifting belt assembly is shown in FIG. 1 on both a male and a female. It will be noted how the belt 10 rides on the upper portion of the pelvis. The shaped lifting belt assembly 10, as noted in FIGS. 2–4, includes a wrap assembly 11, a lumbar panel 12, and side pulls 14 which overlie the shape panel 15 which is intermediate the ends of the wrap assembly and the lumbar panel 12.

Figure 2:
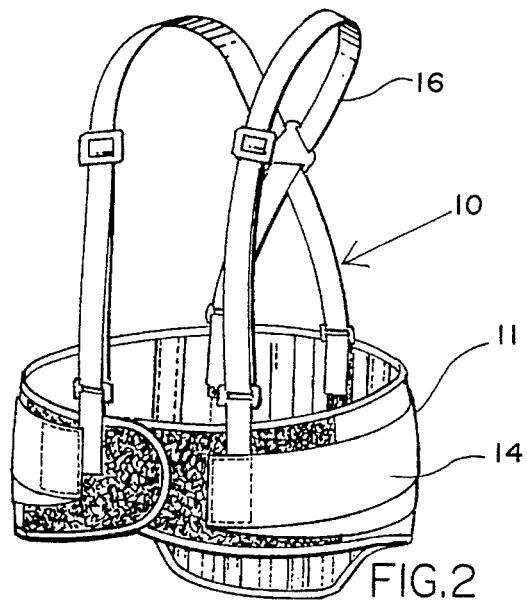
FIG. 2 is a perspective assembled view of the sculptured lifting belt of FIG. 1.
Figure 3:
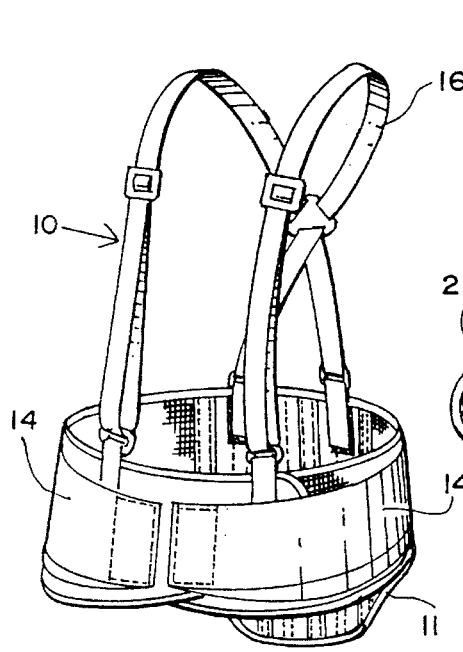
FIG. 3 is another view of the sculptured lifting belt of FIG. 2, but showing the side pulls totally secured.
Figure 4:
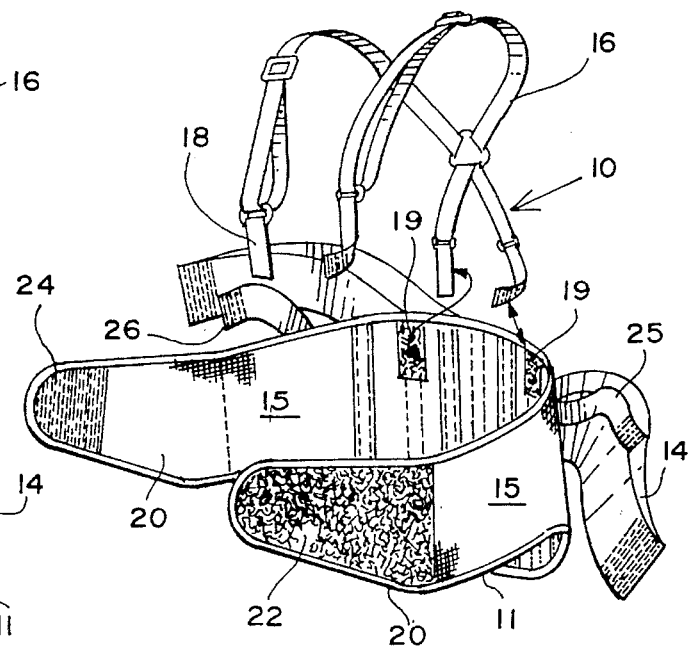
FIG. 4 is an exploded view, partially perspective, showing the shaped lifting belt with the suspender assembly removed, the side pulls removed, the wraps unattached, and the shape straps in place.

The suspender assembly 16 is shown attached in FIGS. 2 and 3 and disassembled in FIG. 4. It will be seen that the suspender ends 18 are provided with hook interior portions, and these are intended to engage the suspender anchors 19 which are a loop fabric for engagement with the hook portion of the suspender ends 18. To be particularly remarked is the fact that the entire suspender assembly 16 is removably secured to the lifting belt assembly 10. This is to accommodate those who prefer not to wear suspenders. This feature also distinguishes the belt of the present invention from much of the prior art where the rear two straps are fixedly engaged with the belt assembly and hence it is awkward to wear the belt without the suspenders.

Turning now to FIG. 5 it will be seen that the wrap 20 extends from the outer lumbar stay 28 to the wrap ends 21 which have a wrap inner loop surface 22. Only four stays are used. Thus the stay 28 runs from top to bottom of the lumbar panel 12 and lumbar panel skirt 13. The shape straps 25 are secured to the outer stay 28 at the upper portion of the lumbar panel. Central stays 29 are on either side of the attachment of the side pull 14 to the lumbar panel 12. One wrap end 24, on the opposite side of the loop surface 22, has a wrap surface hook end 24. A shape strap 25 is provided on either side of the lumbar panel 12 particularly as shown in FIG. 6. The purpose of the shape strap 25 is to shape the shape panel 15 to fit the hips of the wearer.

The lumbar panel 12 differs from most lifting belts in that it has a lumbar panel skirt 13 which depends from the lumbar panel 12 throughout its entire width and extends a distance below an imaginary line 17 which is drawn between the lower portions of the wrap 20 particularly as shown in FIG. 14. The lower edge of the skirt 13 is substantially linear and terminates in the lower curved portion of the shape panel 15. The lumbar panel skirt 13 cooperates with the shape panels 15 to conform to the upper portion of the pelvis in a manner which does not compromise the support aspect of the belt itself but rather enhances the same over a significant portion of the lower lumbar area of the back.

Figure 12:
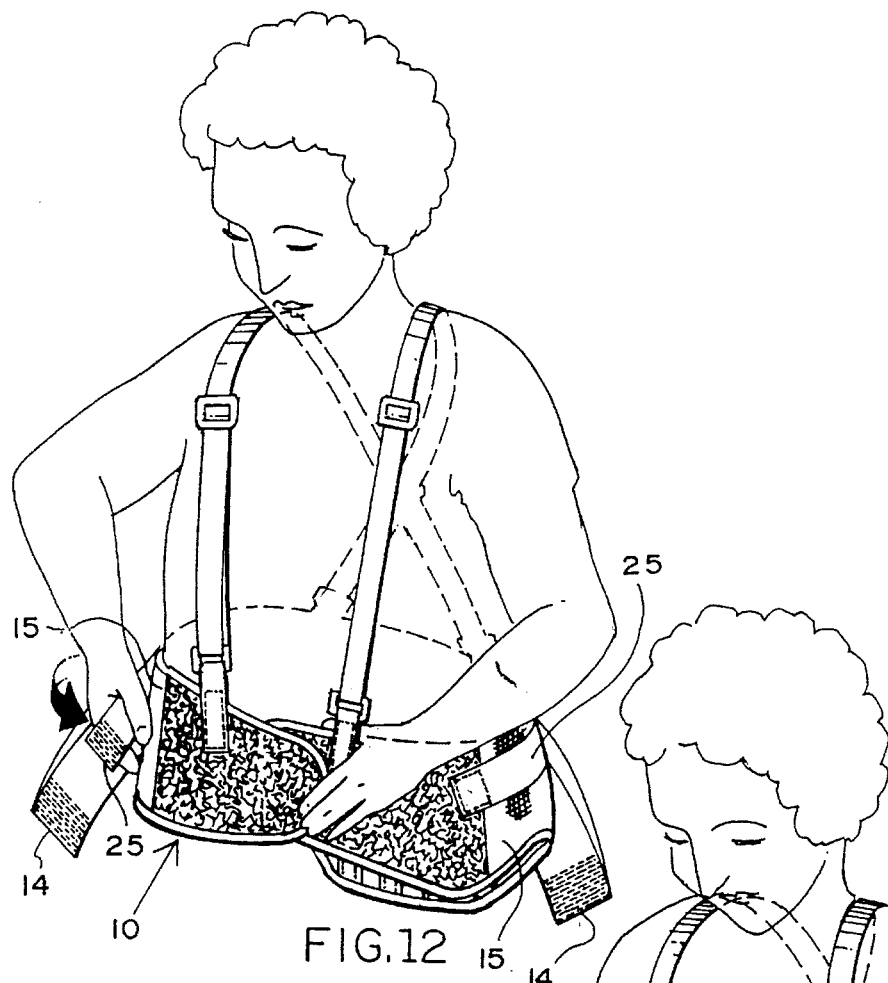
FIG. 12 is a sequential view showing the closing of the side wrap and then securing the shape straps and the side pulls.
Figure 13:
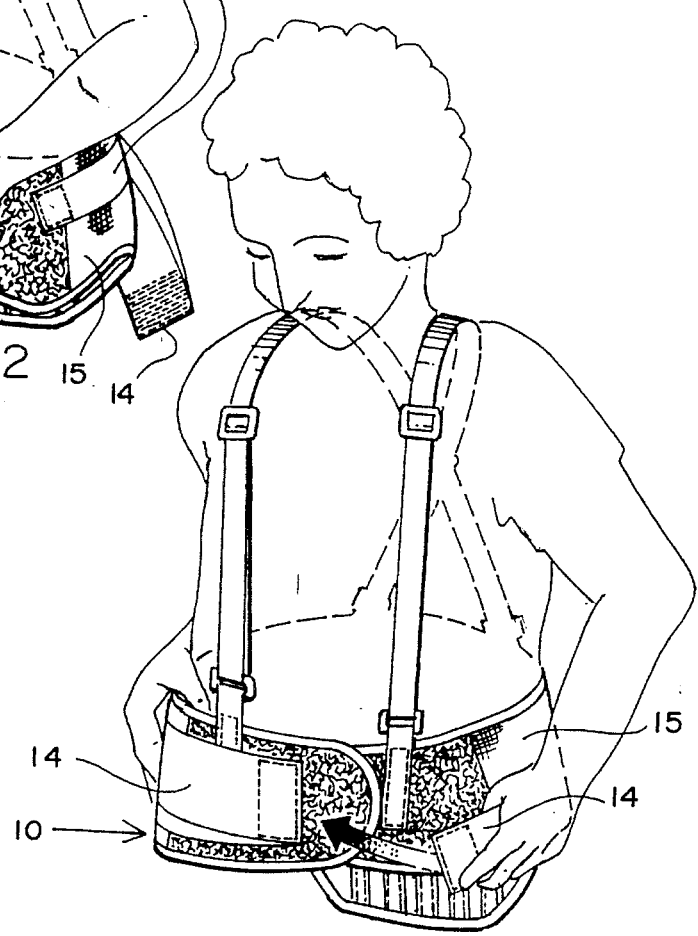
FIG. 13 is a final view of the belt being assembled on the user.

Turning now to FIGS. 8 and 9 it will be seen that the suspender assembly 16 includes a cross portion at the rear and two depending straps from the front which terminate in suspender ends which are of a hook-like material. Loop-like suspender anchors 19 (see particularly FIG. 5) receive and orient the back portion of the suspender. The front portion of the suspender, as shown in FIGS. 10 and 11 can be variably adjusted for securement to the loop wrap surface ends 22. As will be seen in FIG. 11, the shape strap 25 over the left hip of the wearer has already been positioned in place and needs only to be covered by the side pulls 14 when they are centered overlappingly of the ends 18 of the suspender assembly 16. The securement is completed as shown in FIGS. 12 and 13 where finally the side pulls 14 are brought in place.

In the additional FIGS. 14–16, the wrap assembly, lumbar panel, and shape strap are shown with a removable side pull 30 which is substantially identical to the side pull 14 described in the preferred embodiment, but removably secured by side pull hook and loop engaging assembly 35 at the rear central portion of the lumbar panel 12. Desirably the loop portion will be on the removable side pull, and the securement made to the hook portion on the lumbar panel. This is optional, depending upon manufacturing considerations and soiling potential. Nonetheless, the loop material is best secured to the lumbar panel and the hook material to the central portion of the removable side pull 30.

With the removable side pull 31, it can be colored to suit the establishment where it will be used, whether by color, the name of the location, or even the name of the user in those instances where the shaped lifting belt will be personalized. The same is true with regard to the suspender assembly 16.

While the precise materials are not intended to be limiting as to the scope of the present invention, they do serve to illustrate the amount of flexibility, elasticity, and areas of stiffness which are desirable. For example, the lumbar panel 12 is made of Spandex-type material. The stays are stitched from an inelastic-type material to form pockets, and the pockets have stay inserts which are formed of a flexible plastic such as polyvinyl. The side pull straps, two which overlap each other, are formed essentially of elastic material, having end tabs with a removable releasably securable material and relatively inelastic. The wrap assembly includes the outer portions which are relatively inelastic, but the shape panel 15 is formed desirably of Spandex material. The shape straps are slightly elastic, and desirably formed of a woven elastic material. The suspenders are formed of elastic material approximately one inch wide. The wrap assembly has an edge binding of a relatively inelastic material.

While dimensions do not necessarily formed a detail portion of the invention, the ranges in a commercial acceptable unit are helpful in appreciating the invention and recognizing proportions. For example, the overall belt length between small and large will vary from 35½" to 63½". The length of the side pull 14 will vary from 26½" to 40½ on each side. The width of the shaped panel 15 is from six to eight inches, with the distance from top to bottom varying, with the shaped top having a width of five to seven inches, and the shaped bottom having a width of seven to nine inches. Finally, the lumbar panel width will vary between seven inches and 11¾", the height between seven inches and nine inches, and the lumbar curvature width or height between fifteen inches and nineteen inches. The stays are desirably four in number, and the side pull 14 desirably removable for purposes of affording color options for the side pulls 14 and shoulder straps 16.

Although particular embodiments of the invention have been shown and described in full here, there is no intention to thereby limit the invention to the details of such embodiments. On the contrary, the intention is to cover all modifications, alternatives, embodiments, usages and equivalents as fall within the spirit and scope of the present invention, specification and appended claims.

What is claimed is:

1. A shaped lifting belt comprising, in combination:

a wrap assembly, said wrap assembly including a central lumbar panel having an upper outer portion, a central rear portion and lateral edges, and inelastic straps and pockets, said straps having ends;

side pulls, said side pulls being secured at said central rear portion of said lumbar panel and said side pulls having ends with removable attachment means for securing a shape strap;

a stretchable shape panel provided between said lateral edges of said lumbar panel and said ends of said wrap assembly; and substantially inelastic shape straps secured to said upper outer portion of said lumbar panel, said shape straps having a length to span said shape panel and ends for being selectively secured to said wrap ends, whereby a user pulls and secures said shape straps to conform said stretcable shape panels to the torso and upper pelvis, and selectively secures said shape straps to said side pulls' ends.

2. In the shaped lifting belt of claim 1 above, a removable suspender assembly.

3. In the shaped lifting belt of claim 2 above, said suspenders having ends with removable securable material, and said belt having positioned removable securable mating material to adjustably and releasably receive the entire suspender assembly.

4. The shaped belt of claim 1, in which said lumbar panel includes a depending skirt having a lower edge.

5. The shaped belt of claim 4, in which said skirt lower edge is substantially linear and terminates with a curved undercut in the shape panel.

6. A shaped lifting belt comprising, in combination:

a wrap assembly, said wrap assembly including a central lumbar panel having a rear central portion, and upper lateral portions;

stretchable shape panels, said shape panels being formed from substantially elastic material to conform to the torso and hips, and flanking the lumbar panel;

said wrap assembly, lumbar panel and shape panel terminating in wrap ends having inner and outer surfaces, said wrap ends having releasable securable material on both said inner surfaces and an outer surface;

a removable side pull having an end including an interior surface, removable securable material at said central portion, and an elastic section between said removable securable material and the ends of said side pull;

said removable side pull terminating with releasable material on said interior surface; and shape straps having ends, said shape straps extending from said upper lateral portion of said lumbar panel for a distance spanning said shape panel and having removable securable material on said ends thereof for releasable engagement to said inner surface of said wrap ends of said wrap assembly.

7. The method of securing a shaped lifting belt including a wrap assembly having an outer end; a central lumbar panel having a lateral portion and a rear portion, said lumbar panel having side pulls secured thereto at said rear portion; a shape panel, said shape panel being elastic and located between said wrap ends and said lumbar panel; a shape strap, said shape strap being secured to said lateral portion of said lumbar panel and being of sufficient length to engage removable securable material on said warp ends and having less elasticity than said shape panel, said method comprising the steps of:

securing the wrap assembly of a user in overlapping locked relationship to the wrap ends thereof;

pulling the shape straps and removably securing said shape straps to the wrap ends of said wrap assembly;

pulling said side pulls forwardly to a mid-point on an outer end of said wrap assembly at a central portion of the torso of a wearer.

8. In the method of claim 7 above, in which a suspender assembly having four ends with releasable material thereon are provided, applying said suspender assembly to the lift end tap portions prior to adjusting the shape pull and the side pull portions thereof.

* * * * *